United States Patent [19]

Shealy et al.

[11] Patent Number: 4,543,255

[45] Date of Patent: Sep. 24, 1985

[54] CARBOCYCLIC ANALOGS OF PURINE 2'-DEOXYRIBOFURANOSIDES

[75] Inventors: Y. Fulmer Shealy; C. Allen O'Dell, both of Birmingham, Ala.

[73] Assignee: Southern Research Institute, Birmingham, Ala.

[21] Appl. No.: 608,707

[22] Filed: May 10, 1984

[51] Int. Cl.[4] .................. A61K 31/495; A61K 31/52; C07D 239/00
[52] U.S. Cl. .................................... 514/258; 514/261; 514/262; 544/254; 544/276; 544/277
[58] Field of Search ...................... 544/276, 277, 254; 424/180, 253, 250

[56] References Cited

PUBLICATIONS

Journal of Pharmaceutical Sciences, vol. 62, pp. 1432–1434, 1973, Y. F. Shealy and J. D. Clayton.
Journal of Pharmaceutical Sciences, vol. 69, pp. 1019–1021, 1980, H. Lee and R. Vince.

*Primary Examiner*—Alan Siegel
*Attorney, Agent, or Firm*—Roylance, Abrams, Berdo & Goodman

[57] ABSTRACT

There are disclosed carbocyclic analogs of 2-amino-6-substituted-purine 2'-deoxyribofuranosides and 2-amino-6-substituted-8-azapurine 2'-deoxyribofuranosides. The compounds are useful in the treatment of viral infections.

17 Claims, No Drawings

CARBOCYCLIC ANALOGS OF PURINE 2'-DEOXYRIBOFURANOSIDES

BACKGROUND OF THE INVENTION

This invention relates to carbocyclic analogs of 2-amino-6-substituted-purine 2'-deoxyribofuranosides and 2-amino-6-substituted-8-azapurine 2'-deoxyribofuranosides. This invention also relates to the use of such compounds in the treatment of viral infections.

The term "carbocyclic analog of a nucleoside" designates a compound that has the same chemical structure as the nucleoside except that the oxygen atom of the furanose moiety of the nucleoside is replaced by a methylene group in the carbocyclic analog; or, differently expressed, in the carbocyclic analog a cyclopentane ring replaces the tetrahydrofuran ring of the analogous nucleoside. Such nucleoside analogs were designated carbocyclic analogs of nucleosides by Shealy and Clayton, *Journal of the American Chemical Society*, Volume 88, pages 3885–3887, 1966. The natural nucleosides and many of their true nucleoside analogs are subject to the action of enzymes (phosphorylases and hydrolases) that cleave the nuleosides to the pentose and purine or pyrimidine moieties. The biological effects of such true nucleoside analogs may be lessened by the action of these degradative enzymes. In contrast, carbocyclic analogs of nucleosides do not possess the glycosidic bond present in the true nucleosides and, therefore, are not subject of the action of these degradative enzymes. They may also be more selective in their biological actions.

The synthesis of the carbocyclic analog of guanosine (Formula I) was reported earlier by Y. F. Shealy and J. D. Clayton in the *Journal of Pharmaceutical Sciences*, Volume 62, pages 1432–1434, 1973. The carbocyclic analog of guanosine is a carbocyclic analog of a ribofuranoside of a 2-amino-6-substituted-purine. The carbocyclic analogs of 8-azaguanosine (Formula II) and of 2-amino-6-chloro-8-azapurine ribofuranoside (Formula III) were reported in the same article in the *Journal of Pharmaceutical Sciences*. These two compounds are carbocyclic analogs of ribofuranosides of 2-amino-6-substituted-8-azapurines. The preparation in situ and the use of the carbocyclic analog (Formula IV) of 2-amino-6-chloropurine ribofuranoside as an intermediate were reported by Shealy and Clayton (loc. cit.), but the preparation of a pure specimen has been reported. The carbocyclic analogs of three arabinofuranosides of 2-amino-6-substituted-purines and of three arabinofuranosides of 2-amino-6-substituted-8-azapurines were reported by H. Lee and R. Vince (*Journal of Pharmaceutical Sciences*, Volume 69, pages 1019–1021, 1980). These arabinofuranoside analogs either were not active against type 1 herpes simplex virus or were much less active than are the corresponding 2'-deoxyribofuranoside analogs of this invention. The compounds of this invention differ in structure from the arabinofuranoside analogs of Lee and Vince. The 2'-deoxyribofuranoside analogs of this invention do not have a secondary hydroxyl group at the position that corresponds to position 2' of the true nucleosides. Formulas I–IV are set forth below:

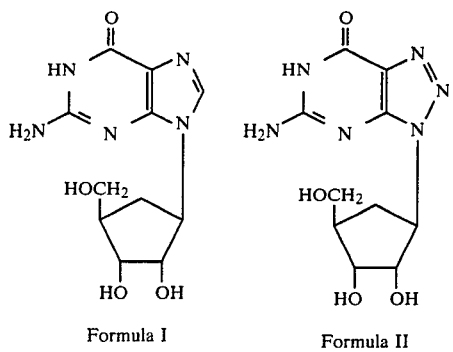

Formula I  Formula II

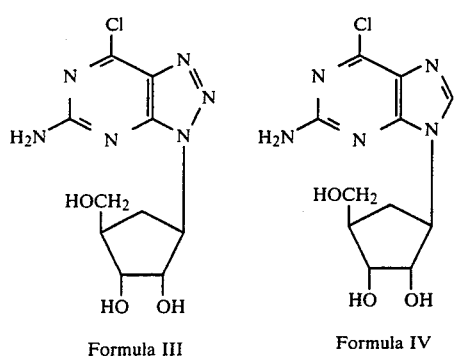

Formula III  Formula IV

SUMMARY OF THE INVENTION

It has now been found that certain carbocyclic analogs of 2-amino-6-substituted-purine 2'-deoxyribofuranosides and of 2-amino-6-substituted-8-azapurine 2'-deoxyribofuranosides are highly active in inhibiting the replication of herpes viruses. Some of these compounds have potent activity against type 2 (genital) herpes simplex virus. Thus, in accordance with this invention, there are provided novel compounds defined by one of the following formulas:

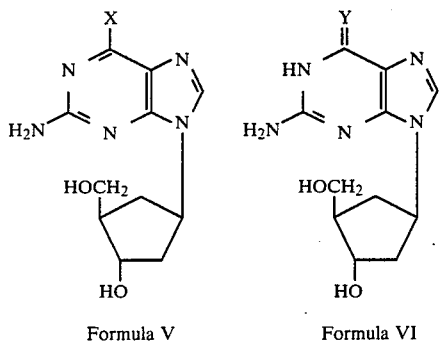

Formula V  Formula VI

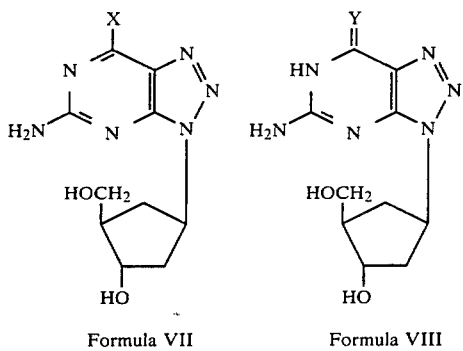

Formula VII        Formula VIII wherein X is halogen, an amino group, an alkylamino group, preferably a lower alkylamino group, an alkoxy group, preferably a lower alkoxy group, or an akylthio group, preferably a lower akylthio group and Y is oxygen or sulfur. By "lower" is meant a group containing from 1 to 6 carbon atoms.

Also, in accordance with this invention, there is administered to a host animal, including man, afflicted with a viral infection a therapeutically effective amount of a compound as defined by Formulas V, VI, VII or VIII.

DETAILED DESCRIPTION OF THE INVENTION

Carbocyclic analogs of 2-amino-6-substituted-purine 2'-deoxyribofuranosides and of 2-amino-6-substituted-8-azapurine 2'-deoxyribofuranosides represented by Formulas V–VIII may be synthesized by beginning with (1α, 2β, 4α)-4-amino-2-hydroxycyclopentanemethanol, or a derivative thereof, and a 2-amino-4-halo-6-substituted-pyrimidine represented by Formula IX;

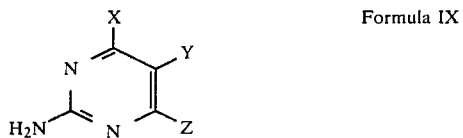

Formula IX wherein X (at position 6) is a halogen, an akylthio group, an alkoxy group, or an hydroxy group (or its oxo tautomer group with a hydrogen on the adjacent ring nitrogen); Y (at position 5) is hydrogen or a group, such as a nitro group or an arylazo group, that is convertible to an amino group; and Z (at position 4) is a halogen. Treatment of a pyrimidine of Formula IX with the aforementioned 4-amino-2-hydroxycyclopentanemethanol produces a pyrimidine of structure X;

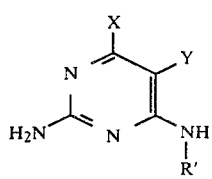

Formula X wherein R' = R" or a derivative thereof and

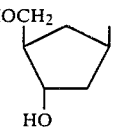

R" = in which the required cyclopentyl group (R') has been positioned in such a way that it will be at position 9 of the target purine. If the starting pyrimidine IX does not have a group (Y) at position 5 that is reducible to an amino group, such a group (Y) is introduced in the next step. A pyrimidine intermediate X in which Y is a reducible group, such as an arylazo group or a nitro group, is then reduced in order to form an amino group (Y=NH$_2$) at position 5. The resulting 2,5-diaminopyrimidine is then treated with a reagent, such as triethyl orthoformate, that forms a purine ring from a 4,5-diaminopyrimidine, and the resulting carbocyclic analog of a 2-amino-6-substituted-purine 2'-deoxyribofuranoside (Formula V or Formula VI) is isolated by typical methods.

The synthesis route is illustrated as follows. Treatment of 2-amino-4,6-dichloropyrimidine (Formula IX with X=Z=Cl and Y=H) with (1α, 2β, 4α)-4-amino-2-hydroxycyclopentanemethanol produces (1α, 2β, 4α)-4-[(2-amino-6-chloro-4-pyrimidinyl)amino]-2-hydroxycyclopentanemethanol (Formula X with X=Cl, Y=H, R'=R"; Example 1). Treatment of the latter compound with an aryldiazonium compound, such as 4-chlorophenyldiazonium chloride, introduces an arylazo group, such as a 4-chlorophenyl azo group (Y=4—ClC$_6$H$_4$N=N—), at position 5. Reduction of the resulting pyrimidine intermediate (e.g., Example 2) with an appropriate reducing agent produces the required 4,5-diaminopyrimidine, illustrated by (1α, 2β, 4α)-4-[(2,5-diamino-6-chloro-4-pyrimidinyl)amino]-2-hydroxycyclopentanemethanol (Formula X with X=Cl, Y=NH$_2$, R'=R"; Example 3). Treatment of the latter 2,5-diaminopyrimidine with triethyl orthoformate followed by treatment of the product successively with aqueous acetic acid and with methanolic ammonia, to liberate derivatized hydroxyl and amino groups, yields the carbocyclic analog of 2-amino-6-chloropurine 2'-deoxyribofuranoside (Formula V with X=Cl; Example 4), which is both a target compound possessing antiviral activity and a precursor of other 2-amino-6-substituted-purine derivatives (Formulas V and VI). Various carbocyclic analogs of 2-amino-6-substituted-purine 2'-deoxyribofuranosides (Formulas V and VI) may be prepared from the 2-amino-6-chloropurine derivative (Formula V, X=Cl). These conversions are illustrated by the preparation of the carbocyclic analog of 2'-deoxyguanosine (Formula VI, Y=O; Example 6) by treating the 2-amino-6-chloropurine (Example 4) with either refluxing aqueous base, or refluxing aqueous acid or, most preferably, refluxing formic acid (88%) and by the preparation of the carbocyclic analogs of 2'-deoxythioguanosine (Formula VI, Y=S; Example 7) and of 2,6-diaminopurine 2'-deoxyribofuranoside (Formula V, X=NH$_2$; Example 5) by treating the same 6-chloropurine with, respectively, sodium hydrogen sulfide or ammonia.

Alternatively, the synthesis of certain carbocyclic analogs of Formula V or VI may begin with a pyrimidine (Formula IX) in which substituent X is the same substituent (X) desired at position 6 of the target purine (Formula V or VI). As an illustration, a pyrimidine of Formula IX in which X is OH, or the tautomeric form in which X is an oxo (X=O) function and the hydrogen is attached to the adjacent ring nitrogen, is an appropriate starting pyrimidine for the synthesis of the carbocyclic analog of 2'-deoxyguanosine (Example 6).

Carbocyclic analogs (Formulas VII and VIII) of 2-amino-6-substituted-8-azapurines are synthesized by routes similar to those described above for the synthesis of purines of Formulas V and VI except that a 2,5-diaminopyrimidine (Formula X) is treated with a nitrosating agent to form a 2-amino-6-substituted-8-azapurine. The carbocyclic analog (Formula VII, X=Cl; Example 8) of 2-amino-6-chloro-8-azapurine 2'-deoxyribofuranoside is both a target compound and a precursor of other 8-azapurine derivatives (Formulas VII and VIII). The 2-amino-6-chloro-8-azapurine (Example 8) may be prepared by treating pyrimidine X with X=Cl, Y=NH$_2$, and R'=R" with sodium nitrite in an acidic medium. Other carbocyclic analogs of 2-amino-6-substituted-8-azapurine 2'-deoxyribofuranosides may be obtained by treating the 6-chloro derivative (Example 8) with an appropriate nucleophilic reagent. The 8-azapurines (1,2,3-triazolo-[4,5-d] pyrimidines) of Examples 9, 10, and 11 are illustrative.

The carbocyclic analogs of 2-amino-6-substituted-purine nucleosides and of 2-amino-6-substituted-8-azapurine nucleosides of this invention inhibit the replication of DNA viruses. Certain representatives of Formulas V-VIII have potent antiviral activity and may be useful for the treatment of virus-induced diseases. The antiviral activity of compounds represented by Formulas V-VIII was measured as a virus rating (VR), and the potency (MIC$_{50}$) was determined as the concentration of the tested compound required to inhibit virus-induced cytopathogenic effects in host cells by 50%. Carbocyclic analogs of 2'-deoxyribofuranosides represented by Formulas V-VIII have unequivocal and generally high activity in inhibiting replication of both type 1 herpes simplex virus (HSV-1) and type 2 herpes simplex virus (HSV-2). In the tests versus HSV-1, compounds belonging to these structural classes generally were more active (VR=4-5) and more potent (lower MIC$_{50}$) than was 1-$\beta$-D-arabinofuranosyladenine (Ara-A), an antiviral drug employed in medical practice and used as a positive control in tests of the compounds of this invention. Notable examples are the carbocyclic analogs of 2,6-diaminopurine 2'-deoxyribofuranoside (Example 5), 2'-deoxyguanosine (Example 6), 2'-deoxythioguanosine (Example 7), 2,6-diamino-8-azapurine 2'-deoxyribofuranoside (Example 9), and 2'-deoxy-8-azaguanosine (Example 10). In tests versus HSV-2, the carbocyclic analogs of 2,6-diaminopurine 2'-deoxyribofuranoside, 2'-deoxyguanosine, 2,6-diamino-8-azapurine 2'-deoxyribofuranoside, and 2'-deoxy-8-azaguanosine were equivalent or superior in activity and potency to Ara-A. Antiviral activity by carbocyclic analogs of 2'-deoxyribofuranoside derivatives of 2-amino-6-substituted-purines and of 2-amino-6-substituted-8-azapurines is illustrated by results summarized in Example 12.

The compounds of this invention are illustrated by, but are not limited to, the following examples. The system of designating the orientation of substituents on the cyclopentane ring as $\alpha$ or $\beta$ is that used by *Chemical Abstracts*, beginning with Volume 76, in the Chemical Substance Index. In the examples illustrating syntheses of the compounds of this invention, data were acquired and are reported as follows. Decomposition and melting temperatures (m.p.) were determined in capillary tubes. Ultraviolet spectra (UV) were recorded with a recording spectrophotometer and absorption maxima are reported in nanometers; sh=shoulder. Solutions for ultraviolet spectral determinations were prepared by diluting a 5-ml. aliquot of a water solution to 50 ml. with 0.1 N hydrochloric acid, phosphate buffer (pH 7), or 0.1 N sodium hydroxide. Absorption maxima of these solutions are reported as being determined at pH 1, 7, or 13, respectively. Infrared spectra (IR) were recorded from samples in pressed potassium bromide discs; s=strong, vs=very strong, sh=shoulder, w=weak. Mass spectral data (MS) were taken from low-resolution, electron-impact spectra determined at 70 eV. The peaks listed are those arising from the molecular ion (M), those attributable to the loss of certain fragments (M minus a fragment), and some other prominent peaks. Fragments containing the complete purine or pyrimidine moiety may be designated P plus an atom or group. Nuclear magnetic resonance spectra were determined at 100 MHz for proton ($^1$H NMR) spectra. The internal standard was tetramethylsilane; s=singlet, t=triplet, m=multiplet. Thin-layer chromatography (TLC) was performed on plates of silica gel, and developed plates were examined by ultraviolet light.

EXAMPLE 1

(1$\alpha$, 2$\beta$, 4$\alpha$)-4-[(2-Amino-6-chloro-4-pyrimidinyl)amino]-2-hydroxycyclopentanemethanol (Formula X; X=Cl, Y=H, R'=R")

A solution of 6.56 g. (40 mmol.) of 2-amino-4,6-dichloropyrimidine (Formula IX with X=Z=Cl, Y=H), 2.60 g. (19.8 mmol.) of (1$\alpha$, 2$\beta$, 4$\alpha$)-4-amino-2-hydroxycyclopentanemethanol, 4.03 g. of triethylamine (40 mmol.), and 410 ml. of 1-butanol was boiled under reflux for 72 hours. Part of the starting pyrimidine that remained unchanged was recovered in two portions (2.7 g. and 0.9 g., m.p. 216°-219° C.) as the reaction mixture was being concentrated in vacuo. After the second portion had been separated by filtration, the filtrate was concentrated to a dark syrup which was concentrated further by evaporating several portions of methanol from it. The residue was mixed thoroughly with 5:1 chloroform-methanol (10 ml.), and a pale tan solid that formed was collected by filtration, washed with the solvent mixture, and dried in vacuo at 78° C.: yield, 2.63 g. (51%); m.p. 168°-170° C. This material was used in the subsequent step since the UV and IR spectra showed it to be comparable to the analytical sample. Additional crude product was isolated from the filtrate by chromatography on silica gel.

To illustrate further, the crude product obtained similarly from a similar reaction allowed to proceed during 10 days in refluxing ethanol was chromatographed on a column of silica gel with chloroform-methanol (9:1) as eluting solvent. Concentration of the product-containing fractions, located by TLC, left a pale yellow syrup that crystallized from water and dried in vacuo: yield, 46%, m.p. 171°-174° C., sintering at 168°-171° C. (inserted at 70° C., 3° C./min.); UV max 300 nm ($\epsilon$4300), 285 sh, 274 ($\epsilon$8800), 237 ($\epsilon$12,500), 214 ($\epsilon$18,700) at pH 1; 287 ($\epsilon$9900), 238 ($\epsilon$11,000), 212 ($\epsilon$26,400) at pH 7; 286 ($\epsilon$9900), 238 ($\epsilon$10,800) at pH 13; MS (direct-probe temperature, 280° C.), m/e 258 (M), 241 (M−OH), 227 (M−CH$_2$OH), 209 (M−CH$_2$OH−H$_2$O), 171

(PNH+C$_2$H$_4$), 144 (PNH+H); IR (strong and medium-strong bands, 1800–700 cm$^{-1}$ region) 1645, 1575 vs, 1475, 1365, 1160, 1015, 970, 795.

Analysis. Calcd. for C$_{10}$H$_{15}$ClN$_4$O$_2$: C, 46.42; H, 5.84; N, 21.66. Found: C, 46.31; H, 5.94; N, 21.47.

After the desired product is collected by filtration, a by-product may sometimes be isolated from the filtrate residue by slurrying it with a choroform-methanol mixture. The by-product melted at 155° C., resolidified, and remelted at 215°–218° C. Mass spectral and microanalytical data indicated that it has the composition C$_{14}$H$_{17}$Cl$_2$N$_7$O$_2$·H$_2$O.

EXAMPLE 2

(1α, 2β, 4α)-4-[[2-Amino-6-chloro-5-[(4-chlorophenyl)azo]-4-pyrimidinyl]amino]-2-hydroxycyclopentanemethanol (Formula X; X=Cl, Y=—N=N—C$_6$H$_4$—Cl-4, R'=R")

A cold solution (at 0°–5° C.) of 4-chlorobenzenediazonium chloride (prepared from about 421 mg. (3.3 mmol.) of 4-chloroaniline, 0.92 ml. of 12 N hydrochloric acid, 3.2 ml. of water, and 254 mg. of sodium nitrite (3.68 mmol.) in 3 ml. of water) was added dropwise during 0.5 hour to a solution of 776 mg. (3 mmol.) of the pyrimidine product of Example 1, 6.0 g. of sodium acetate trihydrate, 15 ml. of acetic acid, and 15 ml. of water. The mixture was stirred overnight at room temperature, and a yellow crystalline precipitate was collected by filtration, washed with cold water, and dried in vacuo at 56° C.: yield, 1.01 g. (85%); m.p. 236°–240° C. dec. The product was recrystallized from a mixture of dimethylformamide (11 ml.) and water (30 ml.), washed with cold water, and dried in vacuo at 78° C.: weight, 980 mg. (97% recovery); m.p. 238°–240° C. dec. (inserted at 100° C., 3° C./min.); UV max 372 nm ($\epsilon$26,400), 280 ($\epsilon$8000), 239 ($\epsilon$18,200), at pH 1; MS (direct-probe temperature, 50° C.) m/e 396 (M), 378 (M—H$_2$O), 361 (M—Cl), 270 (M—HNC$_6$H$_4$Cl); IR (strong and medium-strong bands, 1800–600 cm$^{-1}$ region) 1630, 1565 vs, 1475, 1460, 1365, 1080, 1045, 825, 780.

Analysis. Calcd. for C$_{16}$H$_{18}$Cl$_2$N$_6$O$_2$: C, 48.37; H, 4.57; N, 21.16. Found: C, 48.44; H, 4.38; N, 21.21.

EXAMPLE 3

(1α, 2β, 4α)-4-[(2,5-Diamino-6-chloro-4-pyrimidinyl)amino]-2-hydroxycyclopentanemethanol (Formula X; X=Cl, Y=NH$_2$, R'=R")

A vigorously stirred mixture of 4.00 g. of the 5-[(4-chlorophenyl)azo] pyrimidine of Example 2, 88 ml. of ethanol, 88 ml. of water, and 8.8 ml. of acetic acid was heated to 70° C. under an atmosphere of nitrogen. Zinc dust (8.2 g.) was added in small portions during 40 min., and the mixture was stirred at 70° C. for 1.5 hours. The solid phase was separated by filtration, the filtrate (plus washings) was concentrated in vacuo to about one-fifth of the original volume, the solution was extracted with ether to remove 4-chloroaniline, the pH of the aqueous layer was raised to 5.9 with 2 N sodium hydroxide, and the mixture was refrigerated. The crystalline product was collected by filtration, washed with cold water, and dried in vacuo at 78° C.: yield, 1.30 g. (47%); m.p. 164°–167° C. dec.; UV max 298 nm ($\epsilon$7800), 237 ($\epsilon$15,800), 210 ($\epsilon$16,000) at pH 1; 304 ($\epsilon$9000), 240 sh, 225 sh, 205 ($\epsilon$19,400) at pH 7; 304 ($\epsilon$9000), 240 sh, 225 sh at pH 13; MS (direct-probe temperature, 20° C.) m/e 273 (M), 256 (M—OH), 255 (M—H$_2$O), 224, 198, 196, 186 (PNH+C$_2$H$_4$) 170, 159 (PNH+H).

Analysis. Calcd. for C$_{10}$H$_{16}$ClN$_5$O$_2$: C, 43.88; H, 5.89; N, 25.58. Found: C, 43.62; H, 5.80; N, 25.18.

A lower-melting from (m.p. 103°–106° C.) was also obtained. A mixture of the two forms melted at the higher temperature.

EXAMPLE 4

(1α, 2β, 4α)-4-(2-Amino-6-chloro-9H-purin-9-yl)-2-hydroxycyclopentanemethanol (Formula V; X=Cl)

Freshly distilled triethyl orthoformate (3 ml.) was added to a solution, chilled to 0° C., of 400 mg. of the 2,5-diaminopyrimidine of Example 3 in 3 ml. of dimethylacetamide. Concentrated hydrochloric acid (0.15 ml.) was added to the cold solution, and the resulting mixture was stirred in a stoppered flask at room temperature for 24 hours. The mixture, containing a solid, was concentrated in vacuo (oil pump, 30° C.) to a red solid. A solution of the solid in 20 ml. of 50% acetic acid was stirred at room temperature for 4 hours, volatile components were evaporated in vacuo, and several portions of ethanol were evaporated from the residue. A solution of the partially solid residue in ammonia-methanol (10% NH$_3$) was stirred at room temperature for 4 hours and then concentrated in vacuo to a red gum (460 mg.). A methanol solution of the residue was divided into three portions and applied to three preparative TLC plates of silica gel. The product bands were scraped from the plates, combined, and extracted (4 hours) in a Soxhlet extractor with ethanol, and the filtered extract was concentrated in vacuo to a solid (375 mg.). A solution of the residue in hot water (3 ml.) was cooled, filtered to remove a slight amorphous precipitate, and diluted with an equal volume of acetonitrile. The solution was concentrated, and a crystalline precipitate was collected by filtration, washed with acetonitrile-water (1:1), and dried in vacuo at 56° C. for 2 hours: weight 94 mg.; m.p. 136°–140° C. Since a higher-melting crystalline form had been obtained earlier from ethanol, this specimen was dissolved in ethanol and the solution was concentrated in vacuo to a white crystalline solid; m.p. 163°–166° C.; TLC, 1 spot (3:1 chloroform-methanol); UV max 314 nm ($\epsilon$7000), 242 ($\epsilon$5600), 219 ($\epsilon$27,300) at pH 1; 307 ($\epsilon$7600), 246 ($\epsilon$4600), 223 ($\epsilon$27,900) at ph 7; 307 ($\epsilon$7400), 246 ($\epsilon$4500), 223 ($\epsilon$27,100) at pH 13; MS (direct-probe temperature, 80° C.), m/e 283 (M), 266 (M—OH), 253, 252 (M—CH$_2$OH), 248 (M—Cl), 236 (M—OH—CH$_2$OH+H), 196 (P+C$_2$H$_4$), 170 (P+2H), 169 (P+H).

Analysis. Calcd. for C$_{11}$H$_{14}$ClN$_5$O$_2$. 0.25H$_2$O: C, 45.84; H, 5.07; N, 24.30. Found: C, 45.57; H, 4.93; N, 23.91.

Concentration to dryness of the acetonitrile-water filtrate from the 94-mg. specimen afforded 253 mg. of a peach-colored solid; TLC revealed two slight impurities, but this material was entirely suitable for conversion to other 2-amino-6-substituted-purine derivatives (Formulas V and VI). Also, specimens of Example 4 that were suitable for conversion to other derivatives were obtained without resorting to preparative TLC as follows. The residue from the methanol-ammonia solution was dissolved in water, the hydroxide form of an anion-exchange resin was added until the pH of the stirred solution stabilized at about 11, a small amount of activated charcoal was added, the mixture was stirred and filtered, and the filtrate (plus water washings) was concentrated to dryness; yields 47–50%; TLC, Example 4 as a major spot + trace amounts of one or two impurities.

EXAMPLE 5

(1α, 2β, 4α)-4-(2,6-Diamino-9H-purin-9-yl)-2-hydroxycyclopentanemethanol (The Carbocyclic Analog of 2,6-Diaminopurine 2′-Deoxyribofuranoside; Formula V, X=NH$_2$)

A solution of 500 mg. of the 2-amino-6-chloropurine of Example 4 in 20 ml. of liquid ammonia was heated for 18 hours at 80° C. in a stainless steel bomb having a glass liner. The bomb was chilled and opened, the ammonia was allowed to evaporate, the residue was dissolved in water, and the hot solution was treated with activated charcoal and filtered. The filtrate, combined with several hot water washes, was concentrated to dryness in vacuo, and the residual solid was recrystallized from water and dried in vacuo at 78° C.: yield, 298 mg. (64%); m.p. 242°–246° C.; TLC, 1 spot (40 or 80 mcg., 3:1 chloroform-methanol or 5:2:3 butanol-acetic acid-water as developing solvent); UV max 292 nm ($\epsilon$9800), 253 ($\epsilon$9500), 218 ($\epsilon$22,600) at pH 1; 280 ($\epsilon$10,500), 255 ($\epsilon$8200), 250 sh, 216 ($\epsilon$29,000) at pH 7; 280 ($\epsilon$10,500), 255 ($\epsilon$8200), 250 sh at pH 13; MS (direct-probe temperature, 150° C.), m/e 264 (M), 247 (M−OH), 234, 233 (M−CH$_2$OH), 217 (M−OH−CH$_2$OH+H), 177 (P+C$_2$H$_4$), 151 (P+2H), 150 (P+H); IR (strong bands, 1800−600 cm$^{-1}$ region) 1665, 1630, 1590 vs., 1475, 1455, 1405, 1030, 785, 635.

Analysis. Calcd. for C$_{11}$H$_{16}$N$_6$O$_2$: C, 49.99; H, 6.10; N, 31.80. Found: C, 49.85; H, 6.20; N, 31.74.

EXAMPLE 6

2-Amino-1,9-dihydro-9-[(1α, 3β, 4α)-3-hydroxy-4-(hydroxymethyl)cyclopentyl]-6H-purin-6-one (The Carbocyclic Analog of 2′-Deoxyguanosine; Formula VI, Y=O)

Method A

A solution of 523 mg. of the 2-amino-6-chloropurine of Example 4 is 25 ml. of 0.5 N NaOH was boiled under reflux for 2 hours, the pH of the solution was adjusted to 7, and the mixture was concentrated to dryness in vacuo. A water solution of the residue was applied to a column containing 80 ml. of Sephadex G-10. The column was eluted with water (0.4 ml./min.), and product-containing fractions (located with a UV monitor and by TLC) were combined and concentrated to dryness in vacuo. The residual solid was triturated with ether, collected by filtration, washed with ether, and dried in vacuo; yield, 160 mg. (33%). A specimen was recrystallized from water: m.p. 248°–250° C. dec. (inserted at 180° C., 3° C./min.); TLC, 1 spot (40 or 80 mcg. applied, butanol-acetic acid-H$_2$O (5:2:3) or 2-propanol-1M ammonium acetate (7:3) as developing solvent); UV max 279 nm ($\epsilon$8400) and 254 ($\epsilon$12,500) at pH 1: 270 sh ($\epsilon$10,200) and 253 ($\epsilon$13,800) at pH 7; 268 ($\epsilon$11,800) and 257 sh ($\epsilon$11,000) at pH 13; MS (direct-probe temperature, 160° C.), m/e 265 (M), 248 (M−OH), 235, 234 (M−CH$_2$OH), 190 (M−75), 178 (P+C$_2$H$_4$), 152 (P+2H), 151 (P+H); IR (cm$^{-1}$) 1725 sh, 1680 vs, 1625 vs, 1600 sh, 1565, 1535, 1480, 1405, 1355, 1160, 1020, 775, 680, other broad or weak bands and shoulders.

Analysis. Calcd. for C$_{11}$H$_{15}$N$_5$O$_3$. 1.5H$_2$O: C, 45.20; H, 6.21; N, 23.96. Found: C, 45.24; H, 5.88; N, 24.35.

The carbocyclic analog of 2′-deoxyguanosine was also isolated by diluting a reaction mixture with water and pouring the filtered solution onto a column of the hydroxide form of an anion-exchange resin (Dowex 1-X8), washing the column with water, and eluting the desired product with 5% acetic acid. The glassy solid remaining after the eluate had been concentrated in vacuo was triturated with ethanol, the resulting solid was stirred with water, the mixture was filtered to remove a small amount of insoluble material, the filtrate was lyophilized, and ethanol was evaporated from the residue; yield, 30%.

Method B

A solution of the 2-amino-6-chloropurine of Example 4 (350 mg.) in 88% formic acid (30 ml.) was boiled under gentle reflux overnight. The reaction solution was filtered and then concentrated in vacuo to a white solid residue. Several portions of water were added to and evaporated from the residue. The resulting residue was dissolved in a solution (20 ml.) of anhydrous ammonia in methanol (10% ammonia), and the resulting solution was stirred at room temperature for 3 days. A white solid precipitated slowly from the solution. The mixture was chilled and filtered, and the white solid was washed with cold methanol and then dried in vacuo at 78° C.: yield, 261 mg. (80%); m.p. 210°–215° C., resolidified, remelted at 246°–250° C. (inserted at 130° C., 3°/min.); TLC (performed as for Method A), 1 spot; HPLC (reverse phase, solvent 95:5 water-acetonitrile), 99.97%; UV max 280 nm ($\epsilon$8100) and 254 ($\epsilon$12,100) at pH 1; 270 sh ($\epsilon$9800) and 253 ($\epsilon$13,100) at pH 7; 268 ($\epsilon$11,200) and 257 sh ($\epsilon$10,900); IR (cm$^{-1}$) 1715 s, 1690 sh, 1640 s, 1600 s, 1570, 1535, 1480, 1390 s, 1165, 1040, 1035, 1020, 780, 685, other bands and shoulders.

Analysis. Calcd. for C$_{11}$H$_{15}$N$_5$O$_3$. 0.5H$_2$O: C, 48.16; H, 5.88; N, 25.54. Found: C, 47.91; H, 5.71; N, 25.55.

Method C

The carbocyclic analog of 2′-deoxyguanosine was also obtained by hydrolyzing the 2-amino-6-chloropurine of Example 4 in refluxing hydrochloric acid (1N, 3.5 hours).

EXAMPLE 7

2-Amino-1,9-dihydro-9-[1α, 3β, 4α)-3-hydroxy-4-(hydroxymethyl)cyclopentyl]-6H-purine-6-thione (The Carbocyclic Analog of 2′-Deoxythioguanosine; Formula VI, Y=S)

Hydrogen sulfide gas was introduced during 1 hour into a solution, kept in an ice bath, of 2.05 g. of sodium methoxide in 50 ml. of anhydrous ethanol. To the resulting solution, under an actone-dry ice condenser, was added a solution of 615 mg. of the 2-amino-6-chloropurine of Example 4 in 10 ml. of anhydrous ethanol. The solution was boiled under reflux for 2 hours and then concentrated to dryness in vacuo. A solution of the residue in water (12 ml.) was acidified to pH 4.3 with 6 N HCl. A white solid precipitated. The mixture was chilled, and the solid was collected by filtration, washed with water, and dried in vacuo at 56° C.: yield, 442 mg. (72%); m.p. 295°–298° C. dec. (darkening above 250° C., capillary inserted at 100° C., 3° C./min.). Recrystallization of the product from water (35 ml.) furnished 399 mg. (65% yield, dried in vacuo at 78° C.): m.p. 295°–299° C. dec. (inserted at 200° C., 3° C./min.);

TLC, 1 spot (40 or 80 mcg., 3:1 chloroform-methanol as developing solvent); UV max 350 nm ($\epsilon$21,600), 263 ($\epsilon$7400), 227 sh, 208 ($\epsilon$25,700) at pH 1; 342 ($\epsilon$25,400), 264 ($\epsilon$7500), 231 ($\epsilon$17,400), 208 ($\epsilon$21,700) at pH 7; 318 ($\epsilon$20,200), 271 ($\epsilon$7000), 252 ($\epsilon$11,500), 222 ($\epsilon$16,300) at pH 13; MS (direct-probe temperature, 400° C.), m/e 281 (M), 264 (M−OH), 251, 250 (M−CH$_2$OH), 234 (M−OH−CH$_2$OH+H), 214, 194 (P+C$_2$H$_4$), 168 (P+2H), 167 (P+H); IR (strong bands, 1800−600 cm$^{-1}$ region) 1640, 1600 vs, 1575 vs, 1555, 1385, 1355, 1175, 1020, 940, 895, 650.

Analysis. Calcd. for C$_{11}$H$_{15}$N$_5$O$_2$S: C, 46.89; H, 5.37; N, 24.86. Found: C, 46.86; H, 5.27; N, 25.21.

EXAMPLE 8

(1α, 2β, 4α)-4-(5-Amino-7-chloro-3H-1,2,3-triazolo[4,5-d]pyrimidin-3-yl)-2-hydroxycyclopentanemethanol (Formula VII; X=Cl)

A solution of 587 mg. (8.51 mmol.) of sodium nitrite in 13 ml. of water was added dropwise to a cold (0° C.) solution of 2.00 g. of the pyrimidine product of Example 3 in 20 ml. of water and 6.7 ml. of acetic acid. The mixture was stirred for 1 hour at 0° C., and the precipitated product was collected by filtration, washed with cold water, and dried in vacuo at room temperature: weight, 1.30 g.; m.p. 140°-148° C. dec. A solution of the product in warm ethanol (32 ml.) was treated with activated charcoal, and the warm filtrate (plus washings) was diluted with cyclohexane (80 ml.). The desired product, which crystallized from the cool solution, was separated by filtration after the mixture had been kept at 5° C. for 4 hours, washed with cyclohexane-ethanol (4:1), and dried in vacuo: yield, 1.125 g. (54%); m.p. 152°-153° C. dec. (inserted at 80° C., 3° C./min.); TLC, 1 spot (2:1 chloroform-methanol); UV max 316 nm, 245-260 infl., 226 at pH 1 and in ethanol; 246 and 286 at pH 13; MS (direct-probe temperature, 280° C.) m/e 284 (M), 267 (M−OH), 254, 239, 237 (M−OH−CH$_2$OH+H), 225, 211, 209 (M−75), 197 (P+C$_2$H$_4$), 171 (P+2H), 170 (P+H), 169 (P).

Analysis. Calcd. for C$_{10}$H$_{13}$ClN$_6$O$_2$: C, 42.18; H, 4.60; N, 29.52. Found: C, 42.43; H, 4.89; N, 29.79.

EXAMPLE 9

(1α, 2β, 4α)-4-(5,7-Diamino-3H-1,2,3-triazolo[4,5-d]pyrimidin-3-yl)-2-hydroxycyclopentanemethanol (The Carbocyclic Analog of 2,6-Diamino-8-azapurine 2′-Deoxyribofuranoside; Formula VII, X=NH$_2$)

A solution of 428 mg. of the 2-amino-6-chloro-8-azapurine of Example 8 in 25 ml. of liquid ammonia was heated for 18 hours at 60° C. in a stainless steel bomb containing a glass liner. The bomb was chilled and opened, and ammonia was evaporated with a current of nitrogen. The residual solid was triturated with water (12 ml.), collected by filtration, washed with cold water, and dried in vacuo at 56° C.: yield, 359 mg. (90%); m.p. 245°-247° C. dec. (inserted at 200° C., 3° C./min.). A second crop of the carbocyclic analog of 2,6-diamino-8-azapurine 2′-deoxyribofuranoside was isolated in the same way from the concentrated filtrate: weight 31 mg. (total yield, 98%); m.p. 244°-246° C. dec. (inserted at 200° C., 3° C./min.). A solution of the two portions in boiling water (35 ml.) was treated with a small amount of activated charcoal, concentrated to about one-half of the original volume, and refrigerated. The white crystalline compound (Formula VII, X=NH$_2$) was separated by filtration, washed with cold water, and dried in vacuo at 56° C.: weight, 350 mg. (92% recovery); m.p. 246°-248° C. dec. (inserted at 200° C., 3° C./min.); TLC, 1 spot (40 mcg., 2:1 chloroform-methanol as developing solvent); UV max 285 nm ($\epsilon$7700), 255 ($\epsilon$9800), 214 ($\epsilon$26,000) at pH 1; 287 ($\epsilon$10,600), 258 ($\epsilon$5800), 223 ($\epsilon$25,800) at pH 7; 287 ($\epsilon$10,700), 258 ($\epsilon$5800), 223 ($\epsilon$26,000) at pH 13; MS (direct-probe temperature, 220° C.), m/e 265 (M), 248 (M−OH), 235, 234 (M−CH$_2$OH), 218 (M−OH−CH$_2$OH+H), 206 (M−CH$_2$OH−N$_2$), 190 (M−75), 178 (P+C$_2$H$_4$), 152 (P+2H), 151 (P+H); IR (strong bands; 1800−600 cm$^{-1}$ region) 1670, 1630, 1600, 1585 vs, 1480 vs, 1420, 1020, 785, 670.

Analysis. Calcd. for C$_{10}$H$_{15}$N$_7$O$_2$: C, 45.27; H, 5.70; N, 36.96. Found: C, 44.92; H, 5.45; N, 36.57.

EXAMPLE 10

5-Amino-3,6-dihydro-3-[(1α, 2β, 4α)-3-hydroxy-4-(hydroxymethyl)cyclopentyl]-7H-1,2,3-triazolo[4,5-d]pyrimidin-7-one(The Carbocyclic Analog of 2′-Deoxy-8-azaguanosine; Formula VIII, Y=O)

A mixture of 65 mg. of the 2-amino-6-chloro-8-azapurine of Example 8 and 3 ml. of 0.25 N NaOH was boiled under reflux for 3.5 hours. The solution was treated with a small amount of activated charcoal and filtered, and the filtrate was acidified to pH 3.8 with 6 N HCl to precipitate the carbocyclic analog of 2′-deoxy-8-azaguanosine. After the mixture had been chilled, the white crystalline solid was collected by filtration, washed with water, and dried in vacuo at 78° C.: yield, 60 mg. (98%); m.p. 196°-199° C. (inserted at 100° C., 3° C./min.); TLC, 1 spot (40 or 80 mcg., 5:2:3 butanol-acetic acid-water or 3:1 chloroform-methanol as developing solvent); UV max 270 nm sh ($\epsilon$8200) and 253 ($\epsilon$11,800) at pH 1; 270 ($\epsilon$8700) and 253 ($\epsilon$11,900) at pH 7; 278 ($\epsilon$11,600) and 255 sh at pH 13; MS (direct-probe temperature, 250° C.), m/e 266 (M), 249 (M−OH), 236, 235 (M−CH$_2$OH), 221, 219 (M−OH−CH$_2$OH+H), 209, 207, 193, 191, 179 (P+C$_2$H$_4$), 165, 163, 153 (P+2H), 152 (P+H), 151 (P); IR (strong bands, 1800−600 cm$^{-1}$ region) 1700 vs, 1650 vs, 1595, 1575 vs, 1540, 1385, 1295, 1040.

Analysis. Calcd. for C$_{10}$H$_{14}$N$_6$O$_3$: C, 45.11; H, 5.30; N, 31.57. Found: C, 45.23; H, 5.16; N, 31.74.

EXAMPLE 11

5-Amino-3,6-dihydro-3-[(1α, 3β, 4α)-3-hydroxy-4-(hydroxymethyl)cyclopentyl]-7H-1,2,3-triazolo[4,5-d]pyrimidine-7-thione (Formula VIII, Y=S)

A solution of 284 mg. (1 millimole) of the 2-amino-6-chloro-8-azapurine of Example 8 was added to 12 ml of a solution of sodium hydrogen sulfide (9 millimoles) in absolute ethanol. The solution was boiled under reflux, under a condenser containing an acetone-dry ice mixture, for 2 hours and then concentrated to dryness in vacuo. The residue was dissolved in water (4 ml), and the pH of the solution was adjusted to pH 4.9 by adding 2N hydrochloric acid. A solid, which precipitated, was separated by filtration, washed with water, and dried in vacuo at 56° C.: yield, 136 mg. (48%). A second crop of product was obtained from the filtrate and was washed and dried similarly: yield, 128 mg. (45%). The total crude product (both crops combined) was recrystallized from water. The crystalline precipitate was collected by filtration from the chilled mixture, washed with water, and dried in vacuo at 78° C.: weight, 180 mg. (64% yield); m.p. 215°–219° C. dec. (capillary inserted at 100° C.); UV max 234 nm ($\epsilon$16,200), 263 ($\epsilon$6800), 339 ($\epsilon$19,800) at pH 1; 233 nm ($\epsilon$14,700), 257 ($\epsilon$6900), 280 sh, 337 ($\epsilon$17,400) at pH 7; 253 nm ($\epsilon$8200), 290 ($\epsilon$8300), 328 ($\epsilon$17,100) at pH 13; MS (direct-probe temperature, 340° C.), m/e 282 (M), 264 (M−H$_2$O), 251 (M−CH$_2$OH), 195 (P+C$_2$H$_4$), 169 (P+2H).

Analysis. Calcd. for C$_{10}$H$_{14}$N$_6$O$_2$S.3/4H$_2$O: C, 40.60; H, 5.28; N, 28.41. Found: C, 40.34; H, 5.01; N, 28.73.

EXAMPLE 12

Antiviral Activity of Carbocyclic Analogs of 2-Amino-6-substituted-purine 2′-Deoxyribofuranosides and of 2-Amino-6-substituted-8-azapurine 2′-Deoxyribofuranosides Carbocyclic analogs (Formulas V–VIII) of 2′-deoxyribofuranoside derivatives of 2-amino-6-substituted-purines and of 2-amino-6-substituted-8-azapurines were tested for antiviral activity against viruses that replicate in mammalian cells growing in cell culture. The results of these tests against herpes simplex viruses are summarized in Table 1. The Virus Rating (VR) is a weighted measurement of antiviral activity determined by the method of Ehrlich et al., *Annals of the New York Academy of Science*, volume 130, pages 5–16, 1965. In tests carried out by this method, a VR of 0.5–0.9 indicates marginal to moderate antiviral activity, and a VR equal to or greater than 1 indicates definite antiviral activity. The higher the value of VR, the greater is the antiviral activity. The MIC$_{50}$ (minimum inhibitory concentration, 50%) is the concentration of a test compound required for 50% inhibition of virus-induced cytopathogenic effects. The 2′-deoxyribofuranoside analogs of Examples 4–10 have unequivocal and selective antiviral activity against both type 1 and type 2 strains of herpes simplex virus. In these tests against HSV-1, Examples 5–10 were more active (higher values of VR) and more potent (lower values of MIC$_{50}$) than was Ara-A. In tests versus HSV-2, Examples 5–10 were superior, or equivalent, to Ara-A in activity and potency. The carbocyclic analogs of 2,6-diaminopurine 2′-deoxyribofuranoside and 2′-deoxyguanosine (Examples 5 and 6, respectively) were markedly more effective than was Ara-A. The corresponding 8-azapurine analogs (Examples 9 and 10) were much more effective against HSV-1 than was Ara-A, and they were at least as effective as Ara-A against HSV-2.

TABLE 1

Antiviral Activity of Carbocyclic Analogs of 2′-Deoxyribofuranosides of 2-Amino-6-substituted-purines and of 2-Amino-6-substituted-8-azapurines[a]

| | Herpes Simplex Virus | | | |
|---|---|---|---|---|
| | Type 1, Strain 377 | | Type 2, Strain MS | |
| Compound | VR | MIC$_{50}$ mcg./ml. | VR | MIC$_{50}$ mcg./ml |
| Example 4; Formula V, X = Cl | 1.9 | 8.1 | 2.0 | 37 |
| Example 5; Formula V, X = NH$_2$ | 4.5 4.7 | 0.6 0.3 | 2.9 | 2.4 |
| Example 6; Formula VI, Y = O | ≥4.6 | <0.3 | 3.7 | 0.8 |
| Example 7; Formula VI, Y = S | 4.9 4.4 | <3.2 1.8 | 1.7 | 32 |
| Example 8; Formula VII, X = Cl | 5.0 4.5 | <1.0 1.6 | 1.9 | 23 |
| Example 9; Formula VII, X = NH$_2$ | 4.0 4.4 | <3.2 2.0 | 2.3 | 10 |
| Example 10; Formula VIII, Y = O | 4.2 | 0.6 | 2.1 | 6.9 |
| Ara—A[b]— | 2.5–3.1 | 6.4–9.8 | 1.6–2.3 | 6.4–30 |

[a]Antiviral evaluations were performed with HSV-1 and HSV-2 replicating either in secondary cultures of rabbit kidney cells or in Vero cells.
[b]9-β-D-Arabinofuranosyladenine was tested as a positive control; the range of values of VR and MIC$_{50}$ came from several tests with either rabbit kidney cells or Vero cells as the host cells.

We claim:

1. A compound having one of the following formulas

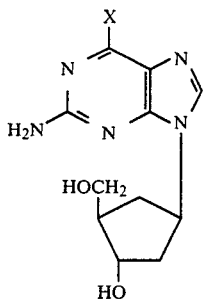

Formula V

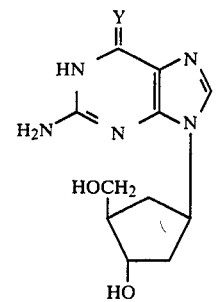

Formula VI

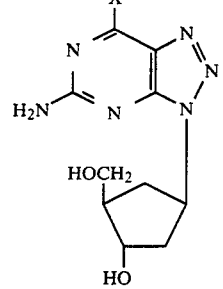

Formula VII

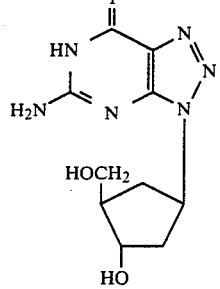

Formula VIII wherein X is halogen, an amino group, an alkylamino group, an alkoxy group, or an akylthio group, and Y is oxygen or sulfur.

2. A compound as defined in claim 1 which is (1α, 2β, 4α)-4-(2-amino-6-chloro-9H-purin-9-yl)-2-hydroxycyclopentanemethanol.

3. A compound as defined in claim 1 which is (1α, 2β, 4α)-4-(2,6-diamino-9H-purin-9-yl)-2-hydroxycyclopentanemethanol.

4. A compound as defined in claim 1 which is 2-amino-1,9-dihydro-9-[(1α, 3β, 4α)-3-hydroxy-4-(hydroxymethyl)cyclopentyl]-6H-purin-6-one.

5. A compound as defined in claim 1 which is 2-amino-1,9-dihydro-9-[1α, 3β, 4α)-3-hydroxy-4-(hydroxymethyl)cyclopentyl]-6H-purine-6-thione.

6. A compound as defined in claim 1 which is (1α, 2β, 4α)-4-(5-amino-7-chloro-3H-1,2,3-triazolo[4,5-d]pyrimidin-3-yl)-2-hydroxycyclopentanemethanol.

7. A compound as defined in claim 1 which is (1α, 2β, 4α)-4-(5,7-diamino-3-H-1,2,3-triazolo[4,5-d]pyrimidin-3-yl)-2-hydroxycyclopentanemethanol.

8. A compound as defined in claim 1 which is 5-amino-3,6-dihydro-3-[(1α, 3β, 4α)-3-hydroxy-4-(hydroxymethyl)cyclopentyl]-7H-1,2,3-triazolo[4,5-d]pyrimidin-7-one.

9. A compound as defined in claim 1 which is 5-amino-3,6-dihydro-3-[(1α, 3β, 4α)-3-hydroxy-4-(hydroxymethyl)cyclopentyl]-7H-1,2,3-triazolo[4,5-d]pyrimidine-7-thione.

10. A process for the treatment of a host animal having a herpes virus infection which comprises administering to said host animal a therapeutically effective amount of a compound represented by one of the following formulas:

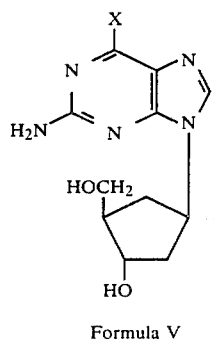

Formula V

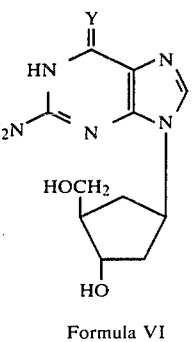

Formula VI

-continued

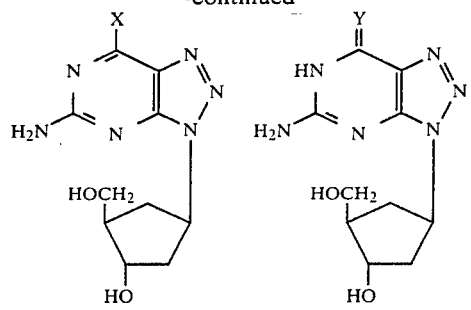

Formula VII

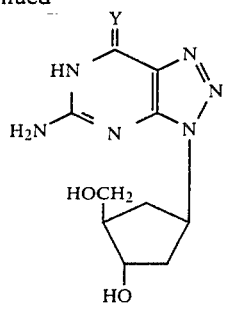

Formula VIII wherein X is halogen, an amino group, an alkylamino group, an alkoxy group, or an akylthio group, and Y is oxygen or sulfur.

11. A process as defined in claim 10 wherein said compound is (1α, 2β, 4α)-4-(2-amino-6-chloro-9H-purin-9-yl)-2-hydroxycyclopentanemethanol.

12. A process as defined in claim 10 wherein said compound is (1α, 2β, 4α)-4-(2,6-diamino-9H-purin-9-yl)-2-hydroxycyclopentanemethanol.

13. A process as defined in claim 10 wherein said compound is 2-amino-1,9-dihydro-9-[(1α, 3β, 4α)-3-hydroxy-4-(hydroxymethyl)cyclopentyl]-6H-purin-6-one.

14. A process as defined in claim 10 wherein said compound is 2-amino-1,9-dihydro-9-[1α, 3β, 4α)-3-hydroxy-4-(hydroxymethyl)cyclopentyl]-6H-purine-6-thione.

15. A process as defined in claim 10 wherein said compound is (1α, 2β, 4α)-4-(5-amino-7-chloro-3H-1,2,3-triazolo[4,5-d]pyrimidin-3-yl)-2-hydroxycyclopentanemethanol.

16. A process as defined in claim 10 wherein said compound is (1α, 2β, 4α)-4-(5,7-diamino-3H-1,2,3-triazolo[4,5-d]pyrimidin-3-yl)-2-hydroxycyclopentanemethanol.

17. A process as defined in claim 10 wherein said compound is 5-amino-3,6-dihydro-3-[(1α, 3β, 4α)-3-hydroxy-4-(hydroxymethyl)cyclopentyl]-7H-1,2,3-triazolo[4,5-d]pyrimidin-7-one.

* * * * *